(12) United States Patent
Rahmer et al.

(10) Patent No.: US 10,890,638 B2
(45) Date of Patent: Jan. 12, 2021

(54) DETERMINATION OF HIGHER ORDER TERMS OF THE THREE-DIMENSIONAL GRADIENT IMPULSE RESPONSE FUNCTION

(71) Applicant: KONINKLIJKE PHILIPS N.V., Eindhoven (NL)

(72) Inventors: Juergen Rahmer, Eindhoven (NL); Tim Nielsen, Eindhoven (NL); Peter Boernert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 13 days.

(21) Appl. No.: 16/391,457

(22) Filed: Apr. 23, 2019

(65) Prior Publication Data

US 2019/0377044 A1    Dec. 12, 2019

(30) Foreign Application Priority Data

Jun. 12, 2018  (EP) ..................... 18177143

(51) Int. Cl.
  *G01R 33/385* (2006.01)
  *A61B 5/055* (2006.01)
  (Continued)

(52) U.S. Cl.
  CPC .......... *G01R 33/3852* (2013.01); *A61B 5/055* (2013.01); *G01R 33/443* (2013.01);
  (Continued)

(58) Field of Classification Search
  USPC ....................................................... 324/309
  See application file for complete search history.

(56) References Cited

U.S. PATENT DOCUMENTS

| 6,066,949 | A | 5/2000 | Alley et al. |
| 2005/0024051 | A1* | 2/2005 | Doddrell ............... A61B 5/7257 324/307 |

(Continued)

OTHER PUBLICATIONS

Alley et al "Gradient Characterization Using a Fourier-Transform Technique" Magnetic Resonance in MED. 39 p. 581-587 (1998).

(Continued)

*Primary Examiner* — Rodney E Fuller

(57) ABSTRACT

A medical instrument includes a magnetic resonance (MR) imaging system with an imaging zone and a gradient coil system with three orthogonal gradient coils.
A processor controls the medical instrument to: repeatedly control the MR imaging system with calibration pulse sequence commands to acquire the MR calibration data for multiples slices using at least one of the three orthogonal gradient coils to generate the slice select gradient magnetic field; compute a Fourier transform of the MR calibration data for each of the voxels of the multiple slices in the phase encoding directions; compute an expansion of the Fourier transformed MR calibration data into spherical harmonics; and calculate a three-dimensional gradient impulse response function for the at least one of the three orthogonal gradient coils using the expansion into spherical harmonics. The calibration pulse sequence commands are configured to acquire MR calibration data from a phantom according to a calibration protocol with two-dimensional phase encoding perpendicular to a slice select gradient magnetic field.

15 Claims, 14 Drawing Sheets

(51) Int. Cl.
*G01R 33/44* (2006.01)
*G01R 33/48* (2006.01)
*G01R 33/483* (2006.01)
*G01R 33/561* (2006.01)
*G01R 33/58* (2006.01)

(52) U.S. Cl.
CPC ..... *G01R 33/4808* (2013.01); *G01R 33/4835* (2013.01); *G01R 33/5611* (2013.01); *G01R 33/58* (2013.01)

(56) References Cited

U.S. PATENT DOCUMENTS

| | | |
|---|---|---|
| 2013/0234708 A1 | 9/2013 | Goora et al. |
| 2016/0063738 A1* | 3/2016 | Saito ................ G01R 33/56316 382/131 |
| 2017/0102439 A1 | 4/2017 | McMillan et al. |

OTHER PUBLICATIONS

S. J. Vannesjo et al., "Gradient system characterization by impulse response measurements with a dynamic field camera," Magn. Reson. Med., vol. 69, No. 2, pp. 583-593, Feb. 2013.

J. H. Duyn, Y. Yang, J. A. Frank, and J. W. van der Veen, "Simple Correction Method for k-Space Trajectory Deviations in MRI," J. Magn. Reson., vol. 132, No. 1, pp. 150-153, May 1998.

N. O. Addy, H. H. Wu, and D. G. Nishimura, "Simple method for MR gradient system characterization and k-space trajectory estimation," Magn. Reson. Med., vol. 68, No. 1, pp. 120-129, Jul. 2012.

E. K. Brodsky, J. L. Klaers, A. A. Samsonov, R. Kijowski, and W. F. Block, "Rapid measurement and correction of phase errors from B 0 eddy currents: Impact on image quality for non-cartesian imaging," Magn. Reson. Med., vol. 69, No. 2, pp. 509-515, Feb. 2013.

A. E. Campbell-Washburn, H. Xue, R. J. Lederman, A. Z. Faranesh, and M. S. Hansen, "Real-time distortion correction of spiral and echo planar images using the gradient system impulse response function," Magn. Reson. Med., vol. 75, No. 6, pp. 2278-2285, Jun. 2016.

K. P. Pruessmann, M. Weiger, M. B. Scheidegger, and P. Boesiger, "SENSE: Sensitivity encoding for fast MRI," Magn. Reson. Med., vol. 42, No. 5, pp. 952-962, Nov. 1999.

S. J. Vannesjo et al., "Field camera measurements of gradient and shim impulse responses using frequency sweeps," Magn. Reson. Med., vol. 72, No. 2, pp. 570-583, Aug. 2014.

Rahmer et al "Cross Term and Higher Order Gradient Impulse Response Function Characterizaiton using a Phantom Based Measurement" Proceedings of the International Society for Magnetic Resonance in Med., Jul. 1, 2018.

Alley et al "Gradient Characterization using a Fourier-Transform Technique" Magnetic Resonance in Med. vol. 39m No. 4, Apr. 1, 1998, p. 581-587.

Breuer et al "Controlled Aliasing in Parallel Imaging Results in Higher Acceleration . . . " Magnetic Resonance in Med. vol. 53, No. 3, Jan. 1, 2005 p. 684-691.

* cited by examiner

DETERMINATION OF HIGHER ORDER TERMS OF THE THREE-DIMENSIONAL GRADIENT IMPULSE RESPONSE FUNCTION

This application claims priority to EP Application No. 18177143.7 filed Jun. 12, 2018.

FIELD OF THE INVENTION

The invention relates to magnetic resonance imaging, in particular to the determination of the gradient impulse response function.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by a transmitter coil cause perturbations to the local magnetic field, and RF signals emitted by the nuclear spins are detected by a receiver coil. These RF signals are recorded as magnetic resonance data and may be used to construct the MRI images. The transmitted RF field is referred to as the B1 field.

To differentiate different locations, spatially and temporally dependent gradient magentic fields are superimposed on an imaging zone. Varying the gradient magentic field enables spatial encoding of the RF signals emitted by the nuclear spins. The gradient magnetic fields in conjunction with the radio frequency pulses define paths in k-space along which the magentic resonance data is sampled.

The journal article Alley et. al. "Gradient Characterization using a Fourier-Transform Technique," Magnetic Resonance in Medicine, 39:581-587 (1998) discloses the use of a Fourier transform analysis to directly measure the k-space trajectory produced by an arbitrary gradient waveform.

SUMMARY OF THE INVENTION

The invention provides for a medical instrument, a method, and a computer program product in the independent claims. Embodiments are given in the dependent claims.

Characterization of the spatial and temporal field response of an MRI gradient system to a demand waveform is important for optimizing gradient coil design, for proper system calibration, and thus for achieving optimal image quality. Measurement of the gradient impulse response function (GIRF) is an efficient way for broad-band characterization of the response. While phantom-based methods are typically limited to 1D characterization, 3D characterization approaches based on field probes require expensive additional hardware (field camera) and are inflexible in their use. Embodiments may provide an efficient phantom-based measurement sequence that combines slice selection with phase encoding to deliver 3D spatial information over a large bandwidth.

In one aspect the invention provides for a medical instrument comprising a magnetic resonance imaging system that has an imaging zone. The magnetic resonance imaging system further comprises a gradient coil system for generating a gradient magnetic field within the imaging zone. The gradient coil system comprises three orthogonal gradient coils. That is to say that each of the gradient coils produces a gradient magnetic field that is essentially or for practical purposes orthogonal to each other.

The magnetic resonance imaging system further comprises a memory for storing machine-executable instructions and calibration pulse sequence commands. The calibration pulse sequence commands are configured for acquiring magnetic resonance calibration data from a magnetic resonance imaging phantom within the imaging zone according to a magnetic resonance imaging protocol. The calibration magnetic resonance imaging protocol uses two-dimensional phase encoding perpendicular to a slice select gradient magnetic field. The calibration magnetic resonance imaging protocol is configured for acquiring slices divided into voxels by the two-dimensional phase encoding.

The magnetic resonance imaging system further comprises a processor for controlling the magnetic resonance imaging system. Execution of the machine-executable instructions causes the processor to repeatedly control the magnetic resonance imaging system with the calibration pulse sequence commands to acquire the magnetic resonance calibration data for multiple slices using at least one of the three orthogonal gradient coils to generate the slice select gradient magnetic field. The calibration is as a practical matter may be performed for each of the three gradient coils. Execution of the machine-executable instructions further causes the processor to compute a Fourier transform of the magnetic resonance calibration data for each of the voxels of the multiple slices in the phase encoding direction.

Execution of the machine-executable instructions further causes the processor to compute an expansion of the Fourier transform magnetic resonance calibration data into spherical harmonics. Execution of the machine-executable instructions further causes the processor to calculate a three-dimensional gradient impulse response function for at least one of the three orthogonal gradient coils using the expansion into spherical harmonics. This embodiment may be beneficial because it may provide for a means of providing for higher order three-dimensional terms of the gradient impulse response functions for the three orthogonal gradient coils. The use of the phase encoding in the two directions perpendicular to the slice select gradient magnetic field chops each slice into a number of smaller volumes. Normally the use of slices in the gradient select direction can only be used for calculating the gradient impulse response function for a single direction three-dimensional higher order terms are not able to be calculated. The use of the two-dimensional spatial phase encoding enables the three-dimensional characterization.

In some embodiments the calibration magnetic resonance imaging protocol may be a thin slice magnetic resonance imaging protocol where the slice separation is selected so that only a few slices need to be acquired and a short scan time results. The slices may be thin to avoid a de-phasing effect. If only two slices are used, the method is also referred to as Duyn's method, which is restricted to determination of the $0^{th}$ and $1^{st}$ order terms only.

In another embodiment the calibration magnetic resonance imaging protocol is configured such that the oblique slices are measured with all three gradient coils active at the same time. This configuration may be used in imaging and may therefore be an additional interaction between the coils which do not occur in isolated operation of a gradient coil.

In another embodiment the memory further contains imaging pulse sequence commands for acquiring magnetic resonance imaging data from the imaging zone according to an imaging magnetic resonance imaging protocol. Execution of the machine-executable instructions further cause the processor to control the magnetic resonance imaging system with the imaging pulse sequence commands to acquire the magnetic resonance imaging data. Execution of the machine-executable instructions further cause the processor to reconstruct a magnetic resonance image from the magnetic resonance imaging data.

In another embodiment the reconstruction of the magnetic resonance imaging comprises correcting the magnetic resonance image using higher order terms of the three-dimensional gradient impulse response function. This embodiment may be beneficial because it may provide for improved quality of the magnetic resonance image.

In another embodiment execution of the machine-executable instructions further causes the processor to correct the imaging pulse sequence commands using the gradient impulse response function for at least one of the three orthogonal gradient coils. This may be affected as correction of dynamic control of the orthogonal coils to suppress a cross-term gradient. This may be determined from looking at the cross-order terms of the three-dimensional gradient impulse response function. Higher order terms, such as the $2^{nd}$ and $3^{rd}$ order terms could be compensated in the same fashion by dynamic control oft higher order shim coils.

In another embodiment execution of the machine executable instructions further causes the processor to correct the imaging pulse sequence commands using the three-dimensional gradient impulse response function for the at least one of the three orthogonal gradient coils by driving orthogonal gradient coils for suppression of cross terms.

In another embodiment execution of the machine executable instructions further causes the processor to correct the imaging pulse sequence commands by adjusting higher order shim coils for the suppression of unwanted higher order response terms.

In another embodiment the magnetic resonance imaging system comprises a radio-frequency system with multiple receive coils.

In another embodiment the calibration magnetic resonance imaging protocol is a SENSE magnetic resonance imaging protocol using the multiple receive coils. This may be beneficial because it may provide for an accelerated measurement of the calibration magnetic resonance imaging data.

In another embodiment execution of the machine-executable instructions causes the processor to adjust the number of the multiple slices and a number of two-dimensional phase encoding steps according to a planned magnetic resonance imaging protocol. This may be beneficial because the calibration of the three-dimensional gradient impulse response function can be planned or adjusted for a particular magnetic resonance imaging protocol. This may be used for adjusting the imaging when the size and position of sub-volumes is changed. This may also be used for image-space combination of signal from different receive channels. In principle, one calibration can be used for all imaging sequences, irrespective of their Field of View (FoV) or resolution. However, if an imaging sequence has problems with eddy currents at certain time constants, it may be beneficial to optimize calibration for that spectral range.

In another embodiment the calibration pulse sequence commands are configured for exciting two or more of the multiple slices simultaneously using multi-band thin-slice excitation. This may be beneficial because it may provide for acceleration of the measurement of the calibration magnetic resonance imaging data.

In another embodiment the magnetic resonance imaging system comprises a dedicated receive coil whose effect on the gradient response is to be tested. This may be beneficial because when this is performed this way the calibration of the three-dimensional gradient impulse response functions automatically takes into account the effect of the dedicated receive coil on the gradient impulse response function. This may have the effect of greatly improving the quality of the magnetic resonance image.

In another embodiment execution of the machine-executable instructions further causes the processor to receive a B0 homogeneity map of the imaging zone. The computation of the Fourier transform of the magnetic resonance calibration data for each voxel of the multiple slices in phase encoding directions is corrected using the B0 homogeneity map. B0 homogeneity may cause errors in the phase encoding. Using the B0 homogeneity map may provide for an improved determination of the three-dimensional gradient impulse response functions.

In another embodiment the medical instrument further comprises any one of the following: a nuclear medicine imaging system, a positron emission tomography system, a single photon emission tomography system, a computer tomography imaging system, a radiotherapy system, and a LINAC system. This embodiment may be beneficial because the additional equipment used for adding additional imaging and/or radiotherapy system may cause differences in the three-dimensional gradient impulse response function.

In another embodiment the calibration magnetic resonance imaging protocol is a gradient pulse magnetic resonance imaging protocol. The gradient pulse sequence may have one active gradient for slice selection and then use the other two gradients for phase encoding. The readout gradient may also use the same gradient as for the slice selection. The gradient pulse magnetic resonance protocol may have a dedicated readout pulse for calibration.

In another embodiment the gradient echo pulse sequence command readout gradient is generated by the slice select gradient. The readout gradient is any one of the following: a Chirp readout gradient, a triangular readout gradient, an alternating combination of a Chirp readout gradient and a triangular readout gradient and a dedicated waveform computed to achieve a maximal spectral intensity at a chosen bandwidth of interest.

In another aspect the invention provides for a method of operating a medical instrument comprising a magnetic resonance imaging system with an imaging zone. The magnetic resonance imaging system comprises a gradient coil system for generating a gradient magnetic field within the imaging zone. The gradient coil system comprises three orthogonal gradient coils. The method comprises repeatedly controlling the magnetic resonance imaging system with the calibration pulse sequence commands to acquire the magnetic resonance calibration data for multiple slices using at least one of the three orthogonal gradient coils to generate the slice select gradient magnetic field.

The calibration pulse sequence commands are configured for acquiring magnetic resonance calibration data from the magnetic resonance imaging phantom within the imaging zone according to a calibration magnetic resonance imaging protocol with two-dimensional phase encoding perpendicular to a slice select gradient magnetic field. The calibration pulse sequence commands are configured for acquiring slices divided into voxels by the two-dimensional phase encoding. The method further comprises computing a Fourier transform of the magnetic resonance calibration data for each of the voxels of the multiple slices in phase encoding directions. The method further comprises computing an expansion of the Fourier transform magnetic resonance calibration data into spherical harmonics. The method further comprises calculating a three-dimensional gradient impulse response function for at least one of the three orthogonal gradient coils using the expansion into spherical harmonics.

In another aspect the invention provides for a computer program product comprising machine-executable instructions for execution by a processor for controlling a medical instrument. The medical instrument comprises a magnetic resonance imaging system with an imaging zone. The magnetic resonance imaging system comprises a gradient coil system for generating a gradient magnetic field within the imaging zone. The gradient coil system comprises three orthogonal gradient coils. Execution of the machine-executable instructions causes the processor to repeatedly control the magnetic resonance imaging system with the calibration pulse sequence commands to acquire the magnetic resonance calibration data from multiple slices using at least one of the three orthogonal gradient coils to generate the slice select gradient magnetic field. The calibration pulse sequence commands are configured for acquiring the magnetic resonance calibration data from a magnetic resonance imaging phantom within the imaging zone according to a calibration magnetic resonance imaging protocol with two-dimensional phase encoding perpendicular to a slice select gradient magnetic field. The magnetic resonance imaging protocol is configured for acquiring slices divided into voxels by the two-dimensional phase encoding.

Execution of the machine-executable instructions further causes the processor to compute a Fourier transform of the magnetic resonance calibration data for at least one of the voxels of the multiple slices in the phase encoding directions. Execution of the machine-executable instructions further cause the processor to compute an expansion of the Fourier transform magnetic resonance calibration data into spherical harmonics. Execution of the machine-executable instructions further cause the processor to calculate a three-dimensional gradient impulse response function for at least one of the three orthogonal gradient coils using the expansion into spherical harmonics.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a 'circuit,' 'odule' or 'system'. Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, random access memory (RAM), read only memory (ROM), an optical disk, a magneto-optical disk, and the register file of the processor. Examples of optical disks include compact disks (CD) and digital versatile disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the interne, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising a 'processor' should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as C or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the internet using an internet service provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE 488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, a tactile electronic display, a Braille screen, a cathode ray tube (CRT), a storage tube, a bi-stable display, an electronic paper, a vector display, a flat panel display, a vacuum fluorescent display (VF), light-emitting diode (LED) displays, an electroluminescent display (ELD), plasma display panels (PDP), a liquid crystal display (LCD), organic light-emitting diode displays (OLED), a projector, and a head-mounted display.

Magnetic Resonance (MR) data is defined herein as being the recorded measurements of radio frequency signals emitted by atomic spins using the antenna of a magnetic resonance apparatus during an MRI scan. Magnetic resonance calibration data and magnetic resonance imaging data are both examples of magnetic resonance data. A magnetic resonance image is defined herein as being the reconstructed two or three-dimensional visualization of anatomic data contained within the MRI data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
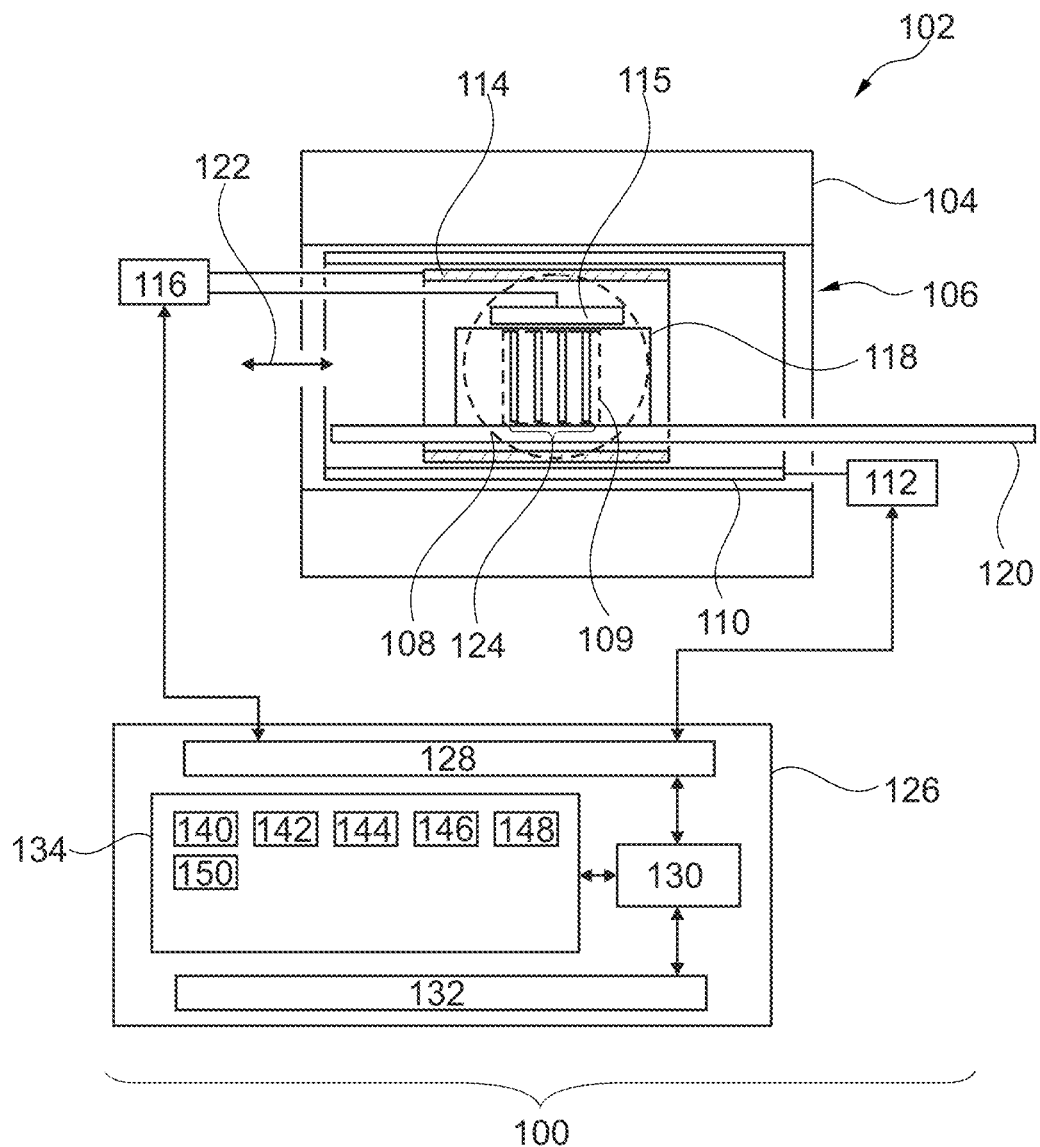
FIG. 1 illustrates an example of a medical instrument.

FIG. 1 illustrates an example of a medical instrument 100. The medical instrument 100 comprises a magnetic resonance imaging system 102. The magnetic resonance imaging system 102 comprises a magnet 104.

The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance imaging data that is typically acquired for the region of interest. A phantom 118 is shown as being supported by a subject support 120 such that at least a portion of the phantom 118 is within the imaging zone 108 and the region of interest 109.

Within the bore 106 of the magnet there is also a set of set of gradient coils 110 which is used for acquisition of preliminary magnetic resonance imaging data to spatially encode magnetic spins within the imaging zone 108 of the magnet 104. The set of gradient coils 110 connected to a magnetic field gradient coil amplifier 112. The set of gradient coils 110 are intended to be representative. The set of gradient coils 110 contain three separate coils for spatially encoding in three orthogonal spatial directions. A magnetic field gradient power supply supplies current to the set of gradient coils. The current supplied to the set of gradient coils 110 is controlled as a function of time and may be ramped or pulsed.

The gradient coils 110 represent three separate sets of orthogonal gradient coils for generating a gradient magnetic field within the imaging zone 108. The z-axis 122 is shown in the figure. The x and y-axes are not depicted. They are orthogonal to each other and the y-axis 122.

The magnetic field gradient coil amplifier 112 is configured for supplying current to each of the sets of gradient coils separately. The magnetic field gradient coil amplifier 112 may have a current sensor system (not depicted) for measuring the current supplied to each of the set of gradient coils 110. The current sensor system could for example be part of the magnetic field gradient coil amplifier 112 or it could also be integrated into the set of gradient coils 110.

Adjacent to the imaging zone 108 is are two radio-frequency coils a body coil 114 and a surface coil 115. Both 114, 115, as mentioned above, may each be used for manipulating the orientations of magnetic spins within the imaging zone 108 and for receiving radio transmissions from spins also within the imaging zone 108. Either radio frequency antenna may contain multiple coil elements. The radio frequency antenna may also be referred to as a channel or antenna. Both radio-frequency coils 114, 115 are connected to a radio frequency transceiver 116. Either radio-frequency coil 114, 115 and radio frequency transceiver 116 may be replaced by separate transmit and receive coils and a separate transmitter and receiver. It is understood that the radio-frequency coils 114, 115 and the radio frequency transceiver 116 are representative. The radio-frequency coils 114, 115 may also represent a dedicated transmit antenna and a dedicated receive antenna. Likewise the transceiver 116 may also represent a separate transmitter and receivers. The radio-frequency coils 114, 115 may also have multiple receive/transmit elements and the radio frequency transceiver 116 may have multiple receive/transmit channels. For example if a parallel imaging technique such as SENSE is performed, either radio-frequency coil 114, 115 could will have multiple coil elements.

Within the bore 106 of the magnet 104 can be seen both a body coil 114 and a surface coil 115. In various examples one or the other or both of these coils 114, 115 may be present. Performing the calibration using the body coil 114 with the surface coil 115 present may be beneficial because the presence of the surface coil 115 may modify the three-dimensional gradient impulse response function. In addition to placing a surface coil 115 in the bore 106 various other equipment or fixtures may also be placed there.

A magnetic resonance phantom 118 has been placed in the bore 106 of the magnet. The phantom 118 is at least partially within the imaging zone 108. In this example the magnet 104 is cylindrically symmetric and the z-axis 122 is marked. As an example, the z-axis could be selected as the direction for the slice select gradient magnetic field. Within the imaging zone 108 is a region of interest 109. Within the region of interest 109 is a number of slices 124 that are perpendicular to the z-axis 122. The x- and y-axes are not indicated in FIG. 1 but are perpendicular to the z-axis 122. The gradient coils corresponding to the x- and y-directions may be used for the two-dimensional phase encoding of the slices 124

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium.

The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions. The machine-executable instructions 140 enable the processor 130 to control the magnetic resonance imaging system 102 and any other components of the medical instrument 100. The computer memory 134 is further shown as containing calibration pulse sequence commands 142. The pulse sequence commands are configured for controlling the magnetic resonance imaging system 100 to acquire magnetic resonance calibration data 144.

The magnetic resonance calibration data 144 acquired with the calibration pulse sequence commands 142 is shown as being stored in the memory 134. The calibration pulse sequence commands 142 are configured for controlling the magnetic resonance imaging system 102 to acquire the magnetic resonance calibration data 144 according to a calibration magnetic resonance imaging protocol that has two-dimensional phase encoding perpendicular to the slice select gradient magnetic field 122. The calibration magnetic resonance imaging protocol is further configured for acquiring the slices 124 divided into voxels by the two-dimensional phase encoding. The calibration procedure may of course be repeated also for the x- and y-gradients as the slice select gradient.

The memory 134 is further shown as containing a Fourier transform of the magnetic resonance calibration data 146 calculated from the magnetic resonance calibration data 144. The memory 134 is further shown as containing an expansion of the Fourier transform magnetic resonance calibration data into spherical harmonics 148. The memory is then further shown as containing the three-dimensional gradient impulse response function 150 that has been calculated from the spherical harmonics 148.

Figure 2:
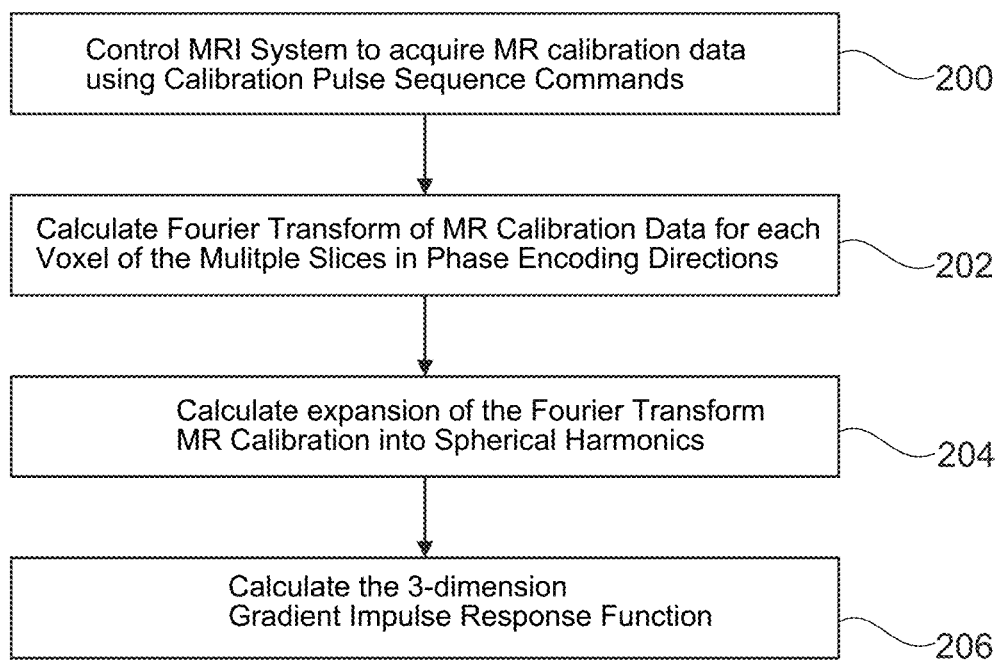
FIG. 2 shows a flow chart which illustrates an example of a method of operating the medical instrument of FIG. 1.

FIG. 2 shows a flowchart which illustrates a method of operating the medical instrument 100 of FIG. 1. First in step 200 the processor 130 repeatedly controls the magnetic resonance imaging system 102 to acquire the magnetic resonance calibration data 144 using the calibration pulse sequence commands 142. Next in step 202 the Fourier transform 146 of the magnetic resonance calibration data is calculated for each of the voxels of the multiple slices in the phase encoding directions. Then in step 204 the expansion 148 of the Fourier transform magnetic resonance calibration data into spherical harmonics is calculated. Finally in step 206 the three-dimensional gradient impulse response function 150 is calculated using the expansion 148.

Figure 3:
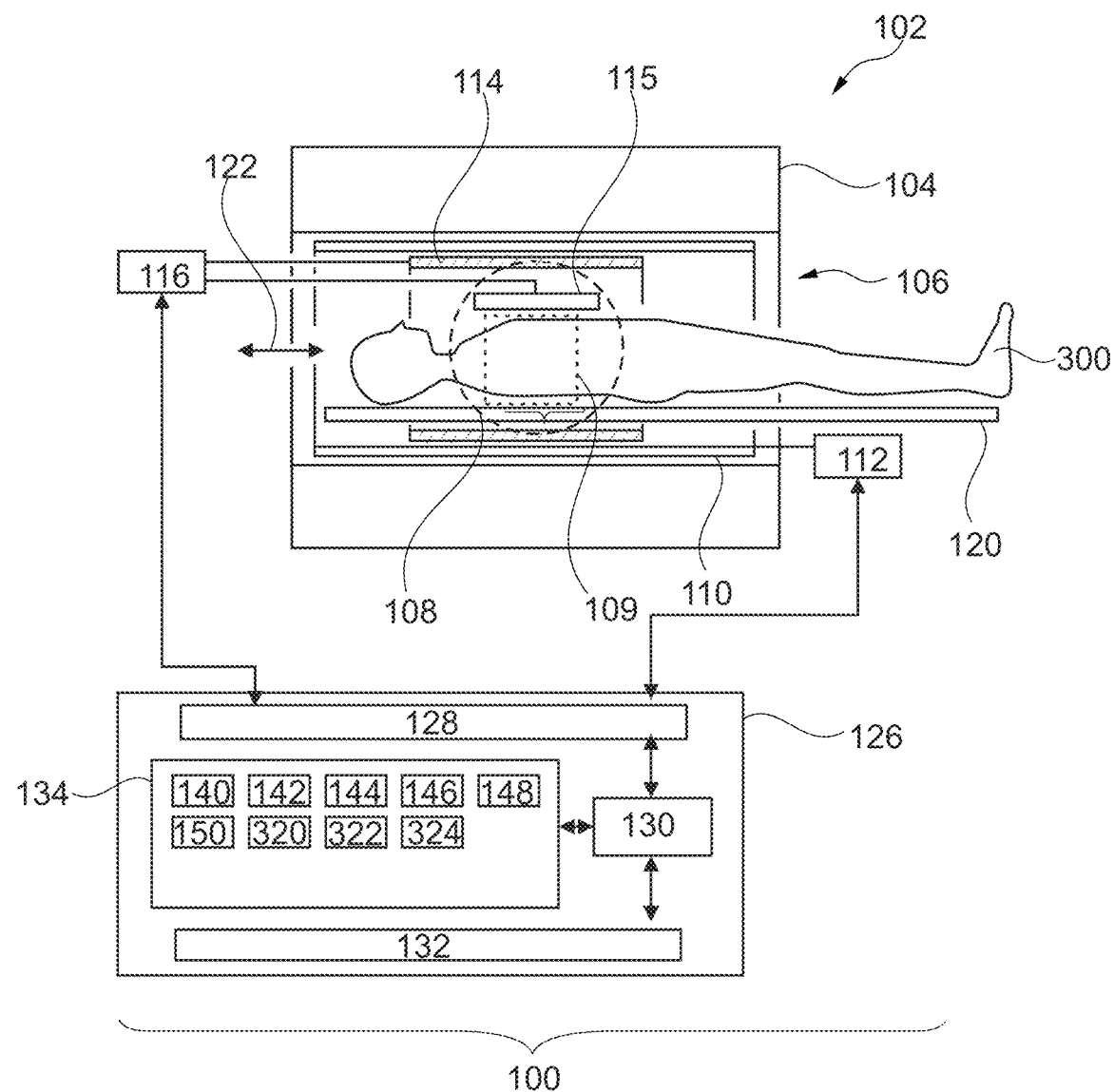
FIG. 3 shows a further view of the medical instrument of FIG. 1.

FIG. 3 shows a further view of the medical instrument 100 of FIG. 1. In this example the phantom 109 has been removed and replaced with a subject 300.

The memory 134 is further shown as containing imaging pulse sequence commands 320. The imaging pulse sequence commands 320 are configured for controlling the magnetic resonance imaging system 102 to acquire magnetic resonance imaging data. The memory 134 is further shown as containing magnetic resonance imaging data 322 that was acquired by controlling the magnetic resonance imaging system 102 with the imaging pulse sequence commands 320. The memory 134 is further shown as containing a magnetic resonance image 324 that was reconstructed from the magnetic resonance imaging data 322.

The three-dimensional gradient impulse response function 150 may be used in several ways for improving the quality of the magnetic resonance image 324. In one example the pulse sequence commands 320 are modified using the three-dimensional gradient impulse response function 150 prior to acquiring the magnetic resonance imaging data 322. For example this could cause a dynamic control of the orthogonal coils to suppress cross-term gradients. The three-dimensional gradient impulse response function 150 contains higher order terms, which could be corrected by dynamic control of the higher order shim coils, so this correction of the pulse sequence may be better than in conventional magnetic resonance imaging systems. Additionally, after the magnetic resonance image 324 has been reconstructed a knowledge of the three-dimensional field generated by the gradient coils 110 can be used to correct distortions in the reconstruction process of the magnetic resonance image 324.

Figure 4:
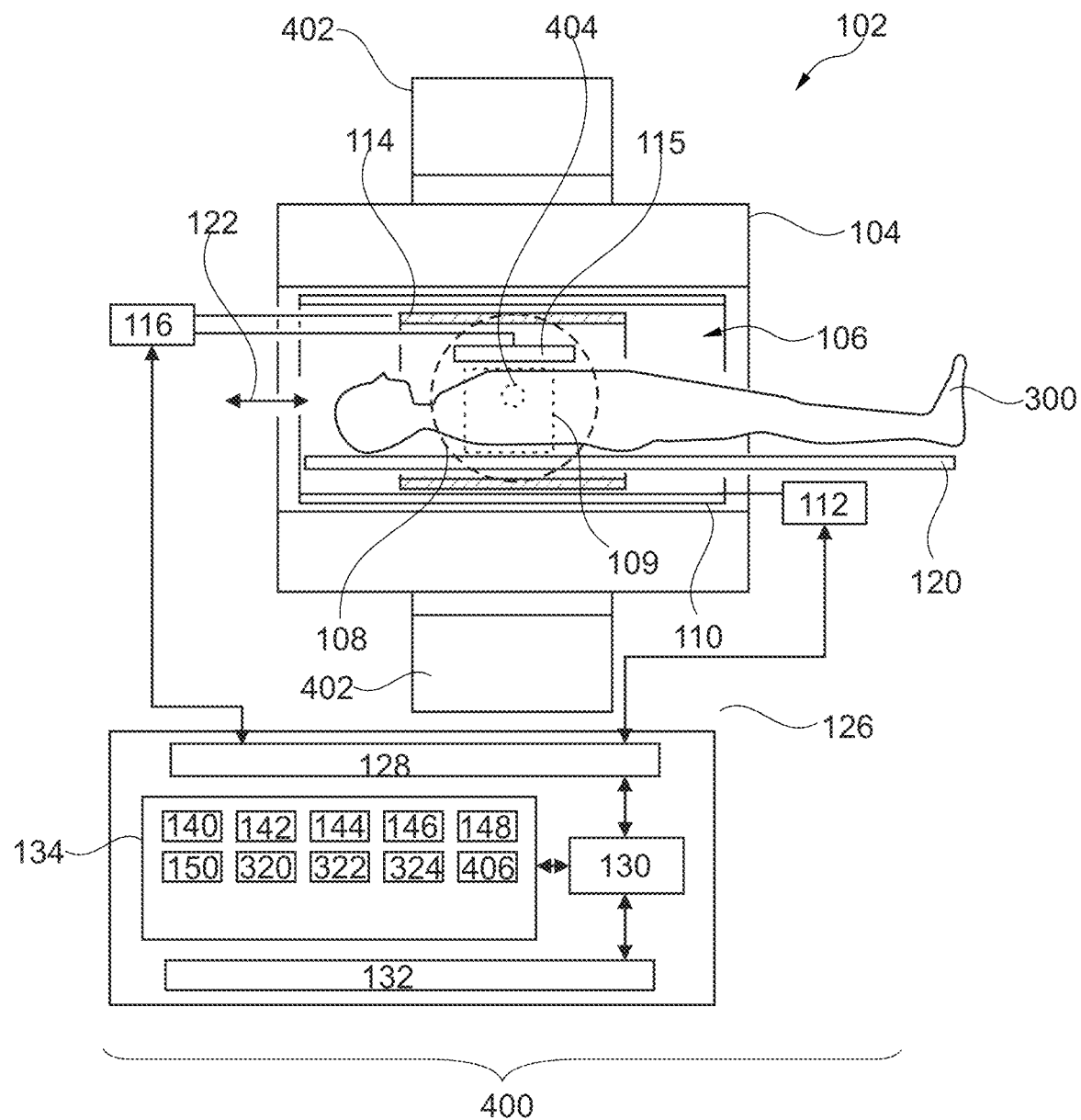
FIG. 4 illustrates a further example of a medical instrument.

FIG. 4 illustrates a further example of the medical instrument 400. The medical instrument 400 is identical with the medical instrument 100 illustrated in FIGS. 1 and 3 except that it additionally contains an additional medical apparatus 402. The medical apparatus 402 could for example be a nuclear medicine imaging system, a positron emission tomography system, a single photon emission tomography system, a computer tomography imaging system, a radiotherapy system, or a LINAC system. There is an additional region 404 within the imaging zone 108. The additional region 404 may be an additional region where medical imaging data is acquired using the medical apparatus 402 or a region which is treated if the medical apparatus 402 is a radiotherapy system or a LINAC system. The memory 134 is further shown as containing control commands 406 which enable the processor 130 to control the operation and function of the medical apparatus 402.

As was previously mentioned, Characterization of the 3D field response of an MRI gradient system is important for proper system calibration to ensure optimal image quality.

One approach is to use image multiple 2D slices of a phantom after application of a test gradient. However, this approach can only characterize long living eddy currents (>~3 ms) because an RF-excitation needs to be inserted between test gradient and data acquisition. Another disadvantage of this method is that it is extremely slow.

A powerful approach to 3D characterization is the acquisition of the gradient impulse response function (GIRF) using a set of distributed MRI probes. It enables expansion of the spatial response pattern into spherical harmonics up to third order or higher.

Drawbacks of this method are:

It requires very expensive additional hardware (the field probes+spectrometer=field camera), Interfacing the field camera with the standard imaging soft/hardware may be difficult (especially with respect to the standard eddy-current compensation/pre-emphasis)

The field probes and their circuitry inside the bore may change the gradient fields and can also affect transmit B1+.

An alternative approach is the phantom-based measurement of the GIRF using a thin slice method. However, this method currently only delivers 0th order information ($\Delta B0$) and 1st order direct terms (Gxx, Gyy, Gzz), but no cross terms (e.g. Gxy) or higher order information.

Yet another method of gradient characterization is a phantom-based method which uses non-selective excitation followed by 3D phase-encoding and application of a test gradient during data acquisition. A main drawback of this method is that the test gradient waveform is coupled to the number of phase-encoding steps which are necessary to avoid intra-voxel dephasing. This coupling severely restricts the usable test gradients or leads to extremely long scan times.

Examples may provide for an extension of the phantom-based thin-slice method by adding 2D phase encoding. This enables characterization of 1st order cross terms as well as higher order spatial components. The method is fast and can also characterize quickly decaying eddy currents. It allows 3D characterization of the gradient response in the true measurement setting: if dedicated receive coils are used, their effect on the gradient response is included in the measurement. Furthermore, undesired effects resulting from the presence of field probes and their circuitry in the bore are avoided. Examples may solves the problem that currently, dedicated field-cameras consisting of a set of local field probes and appropriate spectrometers are necessary for characterization of spatial terms of 2nd order or higher. Characterization of these terms is especially of interest for characterization of gradient coils in hybrid systems, e.g. MR-PET or MR-LINAC system, where necessary compromises have direct effects on image quality. Commercial field cameras are expensive (several hundred thousand Euros), have separate evaluation software and thus require additional interfacing effort with the MRI scanner software, if the measurements are to be used for corrections in reconstruction. In contrast, a phantom based measurement calibration measurement relying on standard MRI sequence software can be easily integrated and be made available for the whole installed scanner base.

Examples may contain one or more of the following features:

Examples may add adds (in-slice) phase encoding to the conventional thin-slice methods for gradient characterization. Using 2D spatial phase encoding, it thus achieves efficient 3D characterization of the gradient response within a rather short phantom scan.

The acquired data are Fourier-transformed along the phase encoding directions yielding the temporal signal evolution for each voxel within a slice.

This may facilitate a couple of additional features:

The conventional thin-slice method depends on good field shimming which is a limiting factor for phantom size and slice positions. With the proposed in-plane spatial encoding, the size of a single voxel (instead of the entire slice) is the effective scale for the shimming requirements. Static field inhomogeneities between voxels can be corrected for retrospectively in the data analysis.

Spatial encoding of subvolumes furthermore enables image-space combination of signal from different receive channels, which is superior to the current channel combination that is based on principal component analysis.

Size and position of subvolumes can be adjusted by changing the number of slices as well as the number of in-slice phase encoding steps.

As slice and subvolume encoding may suffer from a sub-optimal system calibration, an iterative measurement procedure consisting of repeated measurements of the GIRF combined with improving eddy current compensation parameters based on the latest GIRF measurement can be applied.

For the speeding up the proposed phase-encoding, the method can be combined with parallel imaging based on a SENSE scheme.

The method can also be combined with multi-band thin-slice excitation for measuring the GIRF Compared to conventional 1D phantom-based approaches, examples may provide additional phase encode gradients are introduced on the gradient axes orthogonal to the test gradient axis (cf. FIG. 5 below). For evaluation, Fourier transforms are performed along the phase encoding axis, so that the temporal phase evolution is obtained for each encoded subvolume. From the known positions of the subvolumes, the spatial response patterns can be obtained, e.g. by an expansion into spherical harmonics. From the phase evolution, the gradient impulse response function (GIRF) and the respective spectra, the gradient modulation transfer functions (GMTF), can be obtained using standard processing described elsewhere. The GMTF is the Fourier transform of the GIRF.

Figure 5:
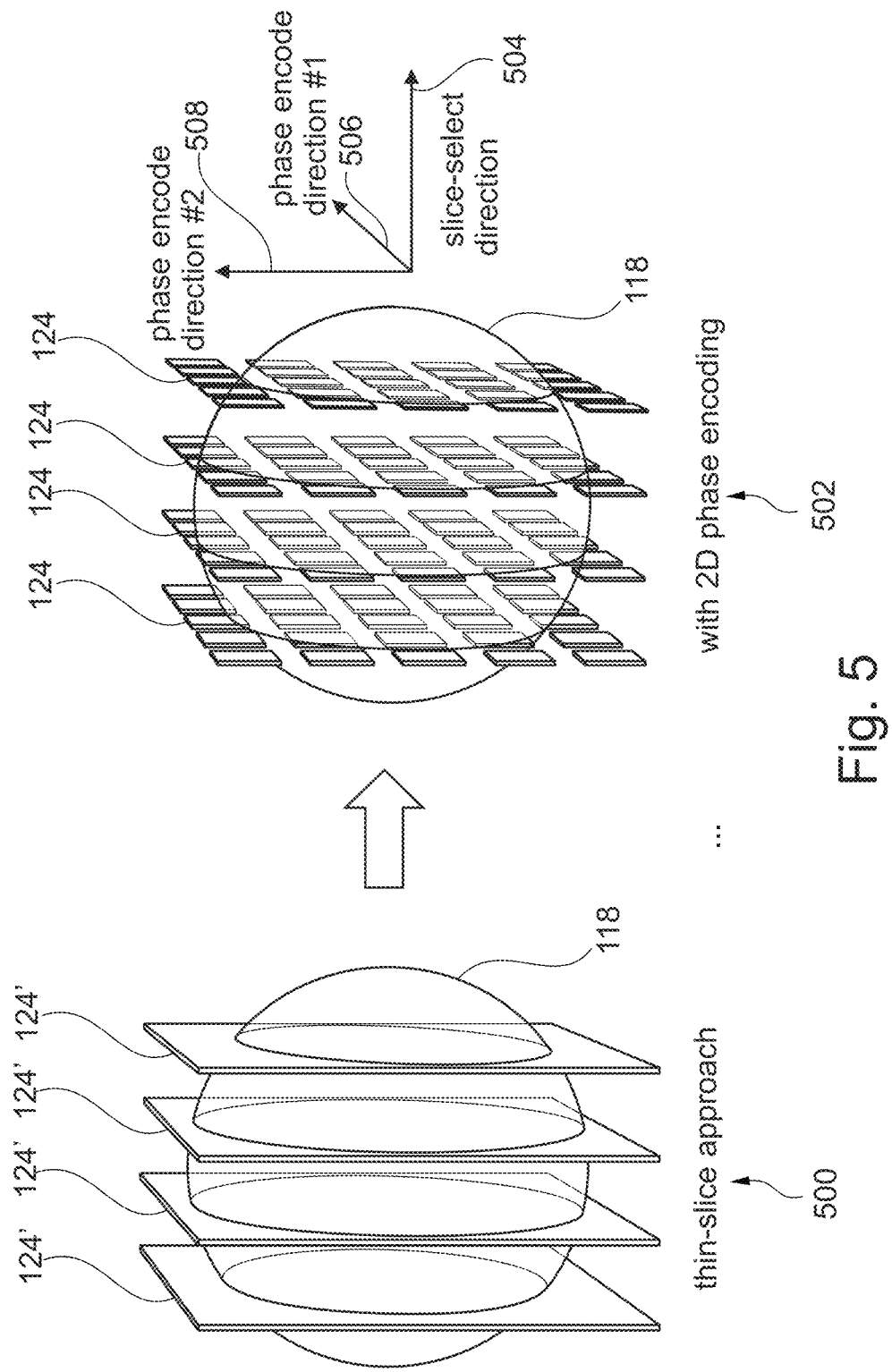
FIG. 5 compares the slice selection for the measurement of gradient impulse response functions with and without using two-dimensional phase encoding

FIG. 5 shows two images. The first image 500 illustrates the conventional thin slice approach 500 to calculating a gradient impulse response function, 502 illustrates the thin slice approach with two-dimensional phase encoding for calculating a three-dimensional gradient impulse response function. In the image 500 the phantom 118 is imaged using several slices 124' that do not have phase encoding. In image 500 in addition to the slice select direction 504 there is phase encoding in two directions 506, 508 within each of the slices 124. This effectively divides each of the slices 124 into multiple voxels.

Figure 6:
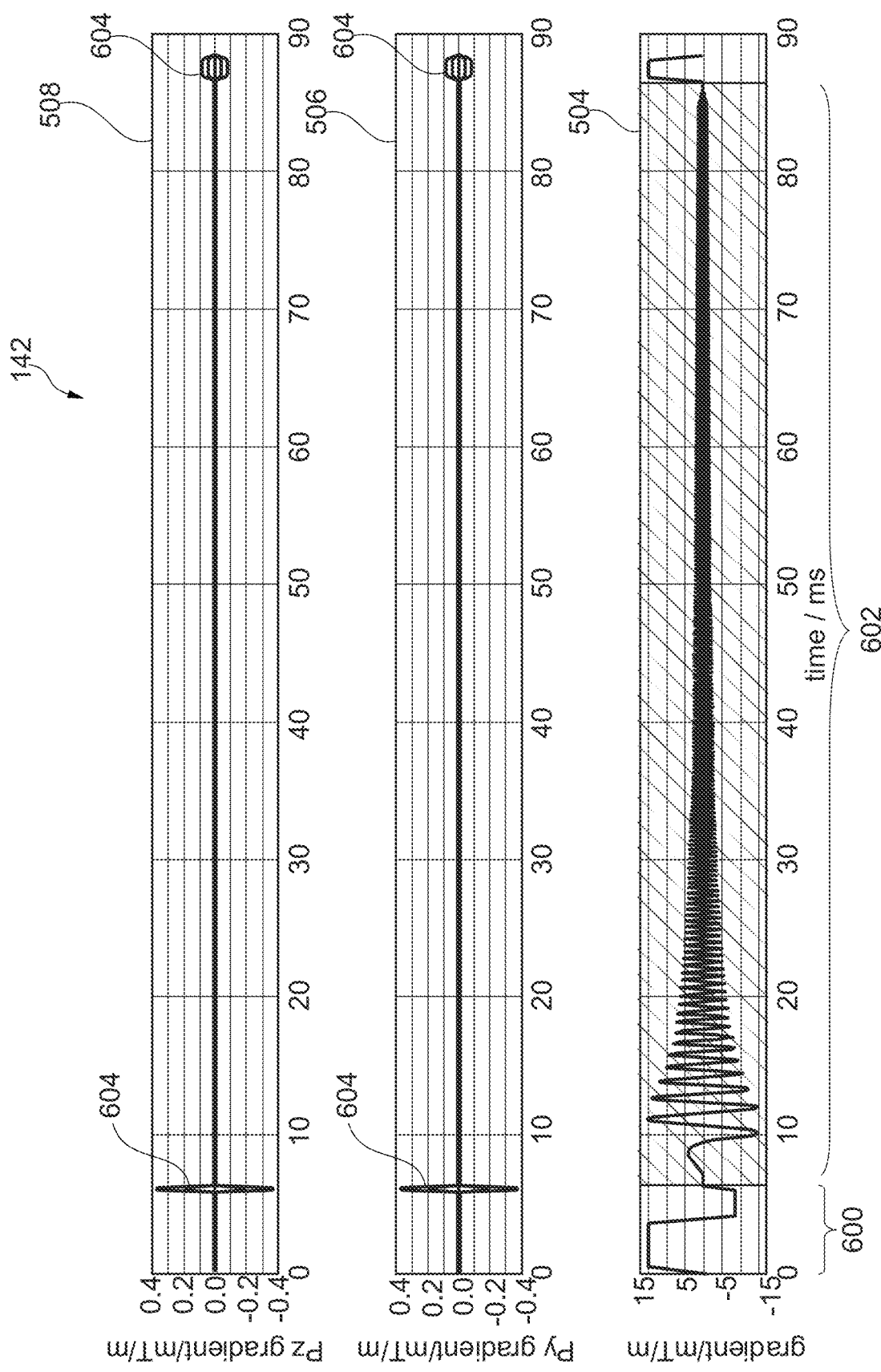
FIG. 6 illustrates a portion of a pulse sequence for measuring the gradient impulse response function and its higher order terms.

FIG. 6 shows an example of calibration pulse sequence commands 142. In this timing diagram we see the timing diagram for the gradient in the slice select direction 504 and also in the two phase encoding directions 506 and 508. The slice selection direction pulse gradient 504 comprises a slice select gradient pulse 600 and a readout gradient pulse 602 for probing the response of the gradient system. The gradients for the phase encoding 506 and 508 both comprise phase encoding gradient pulses 604. The pulse sequence in FIG. 6 is a partial pulse sequence and shows only the gradients of a single readout, which needs to be repeated for all phase encoding steps, slices, and gradient orientations for a complete GIRF calibration sequence.

Figure 7:
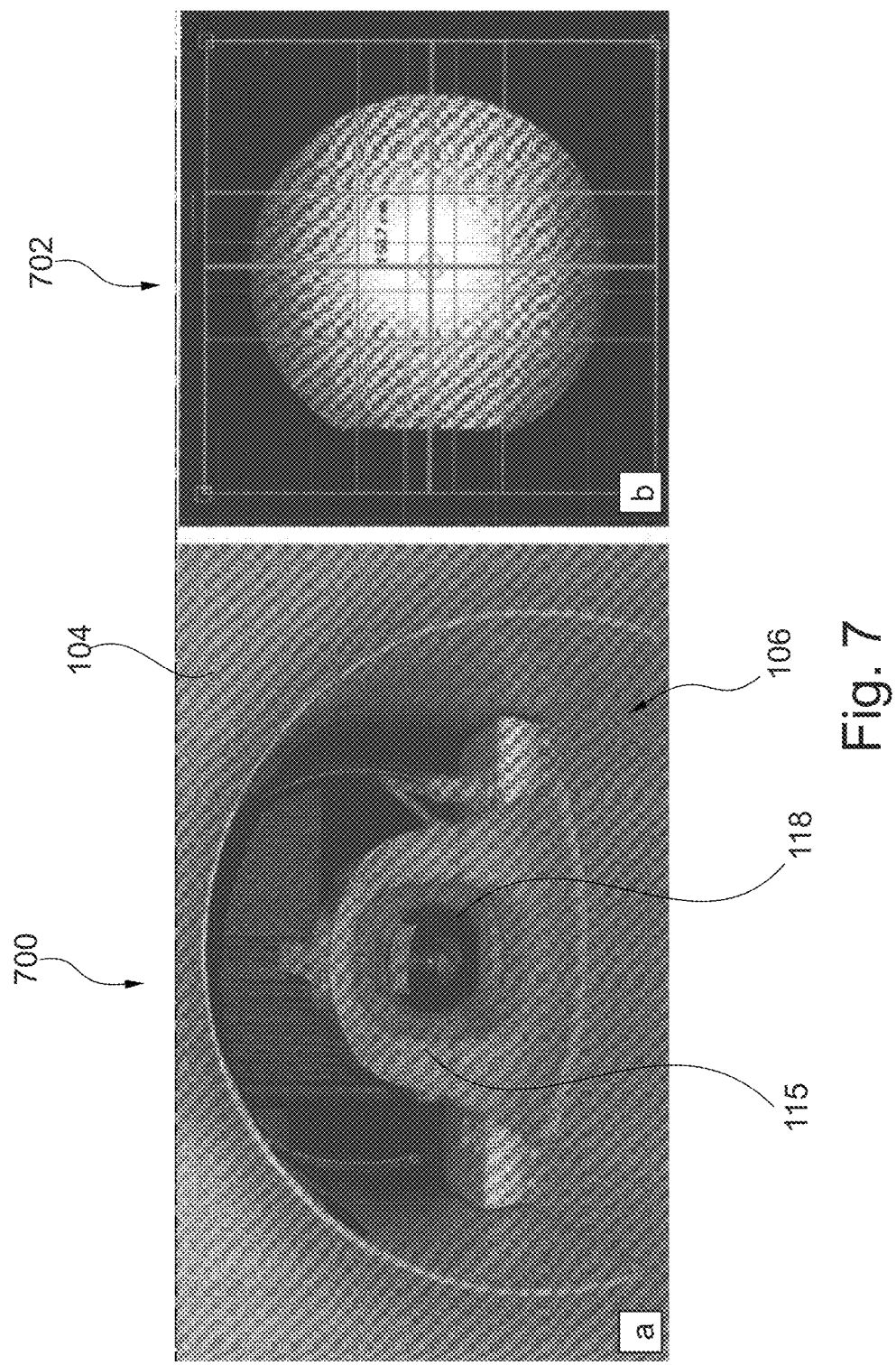
FIG. 7 shows a photograph of a phantom in a magnetic resonance imaging system and slice selection of the phantom for measuring the gradient impulse response function.

FIG. 7 shows two images. Image 700 is a photograph of a phantom in the magnetic resonance imaging system 102. Image 702 shows a diagram illustrating the slice selection for the phantom 118 shown in photograph 700.

FIGS. 8 to 10 and FIGS. 11 to 14 show 1st order cross terms and selected 2nd and 3rd order terms respectively. This information is comparable to what can be obtained using a hardware field camera and can be used for broadband gradient chain characterization up to higher spatial orders.

Figure 8:
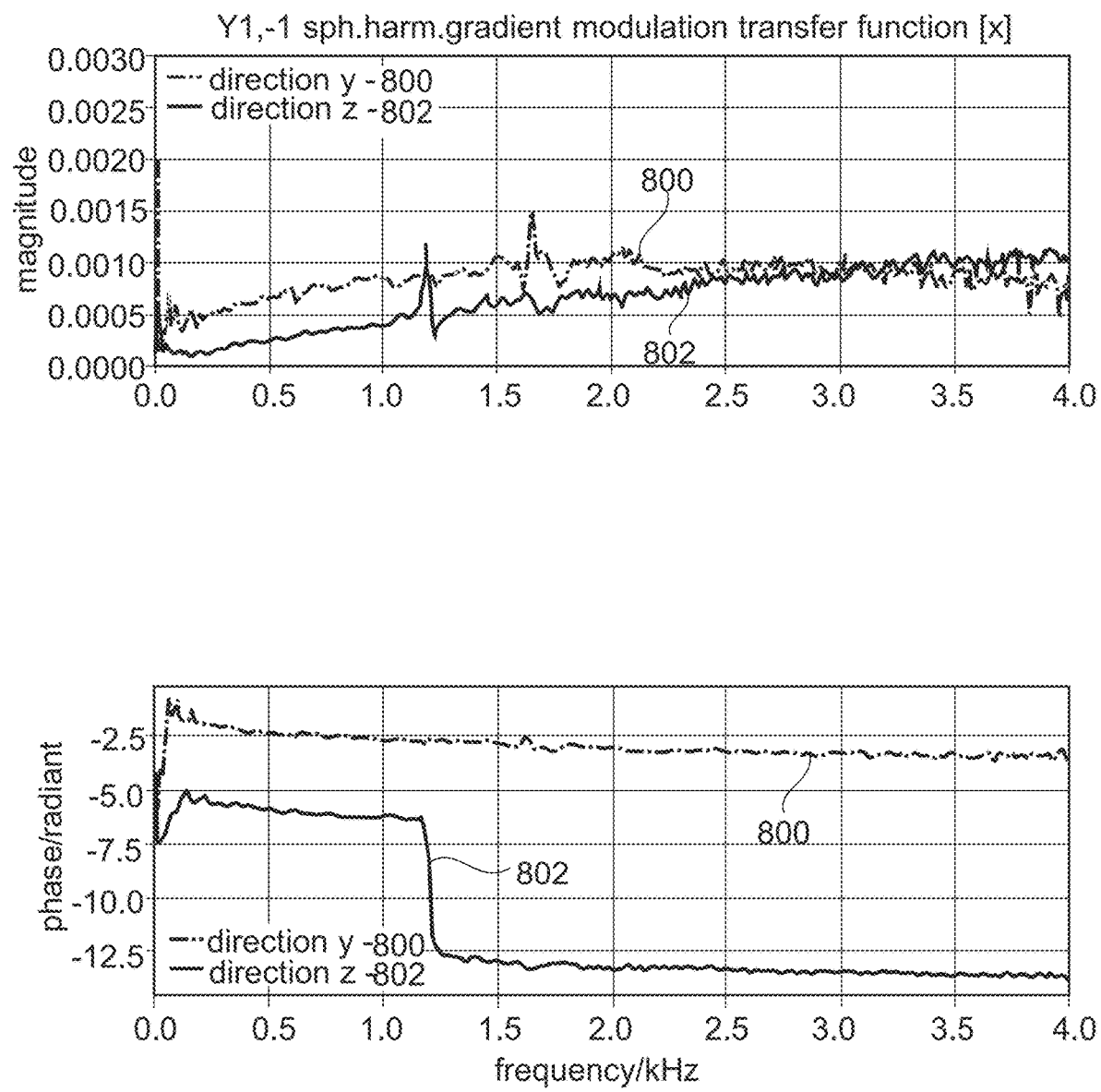
FIG. 8 plot of the phase and amplitude for the $Y_{-1}^{1}$ term of the gradient impulse transfer function, which is the $1^{st}$ order cross term in x direction upon y and z channel excitation.
Figure 9:
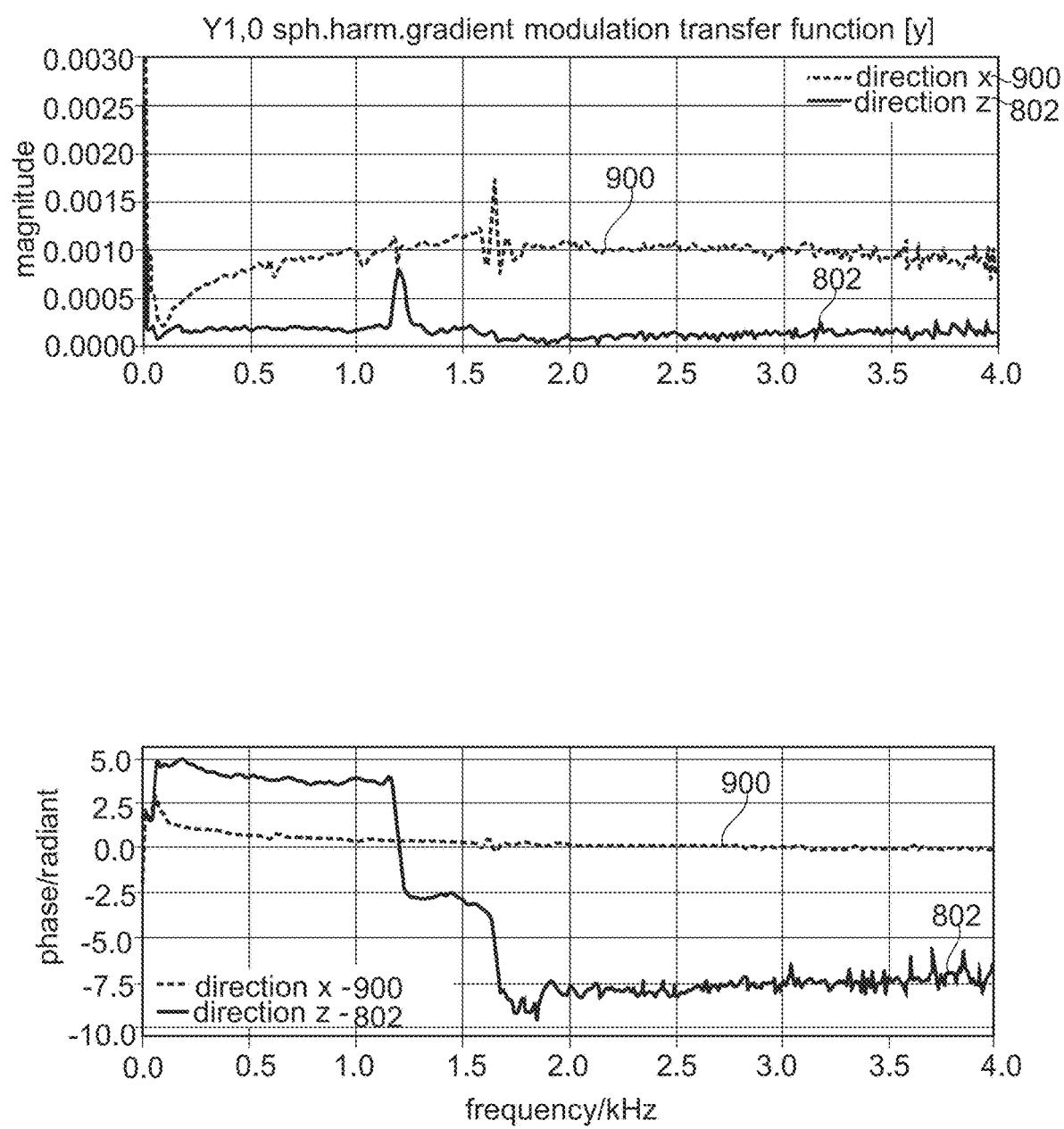
FIG. 9 plot of the phase and amplitude for the $Y_{0}^{1}$ term of the gradient impulse transfer function, which is the $1^{st}$ order cross term in y direction upon x and z channel excitation.
Figure 10:
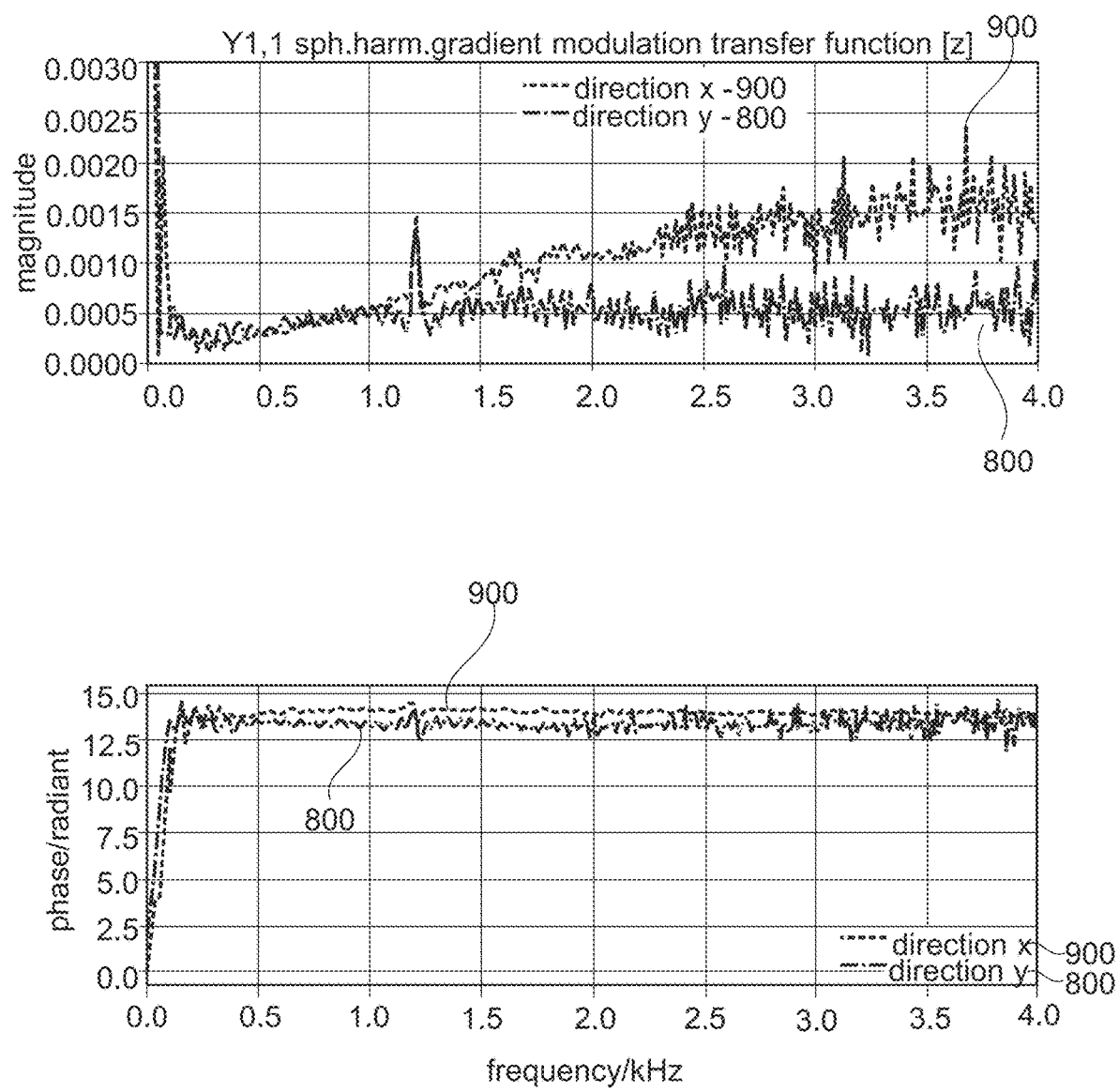
FIG. 10 plot of the phase and amplitude for the $Y_1^1$ term of the gradient impulse transfer function, which is the 1$^{st}$ order cross term in z direction upon x and y channel excitation.
Figure 11:
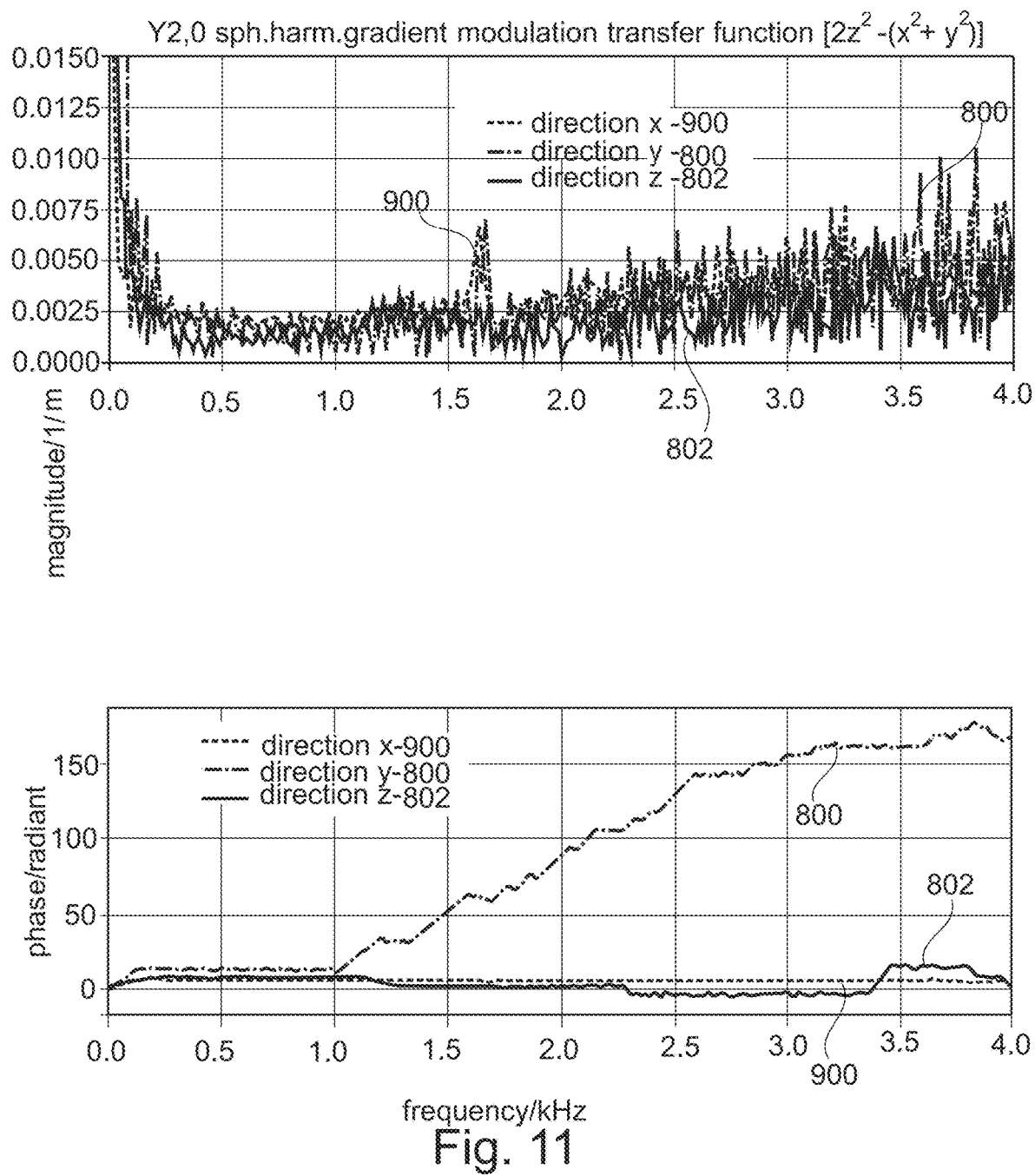
FIG. 11 plot of the phase and amplitude for the $Y_0^2$ term of the gradient impulse transfer function for excitation on all three gradient channels.
Figure 12:
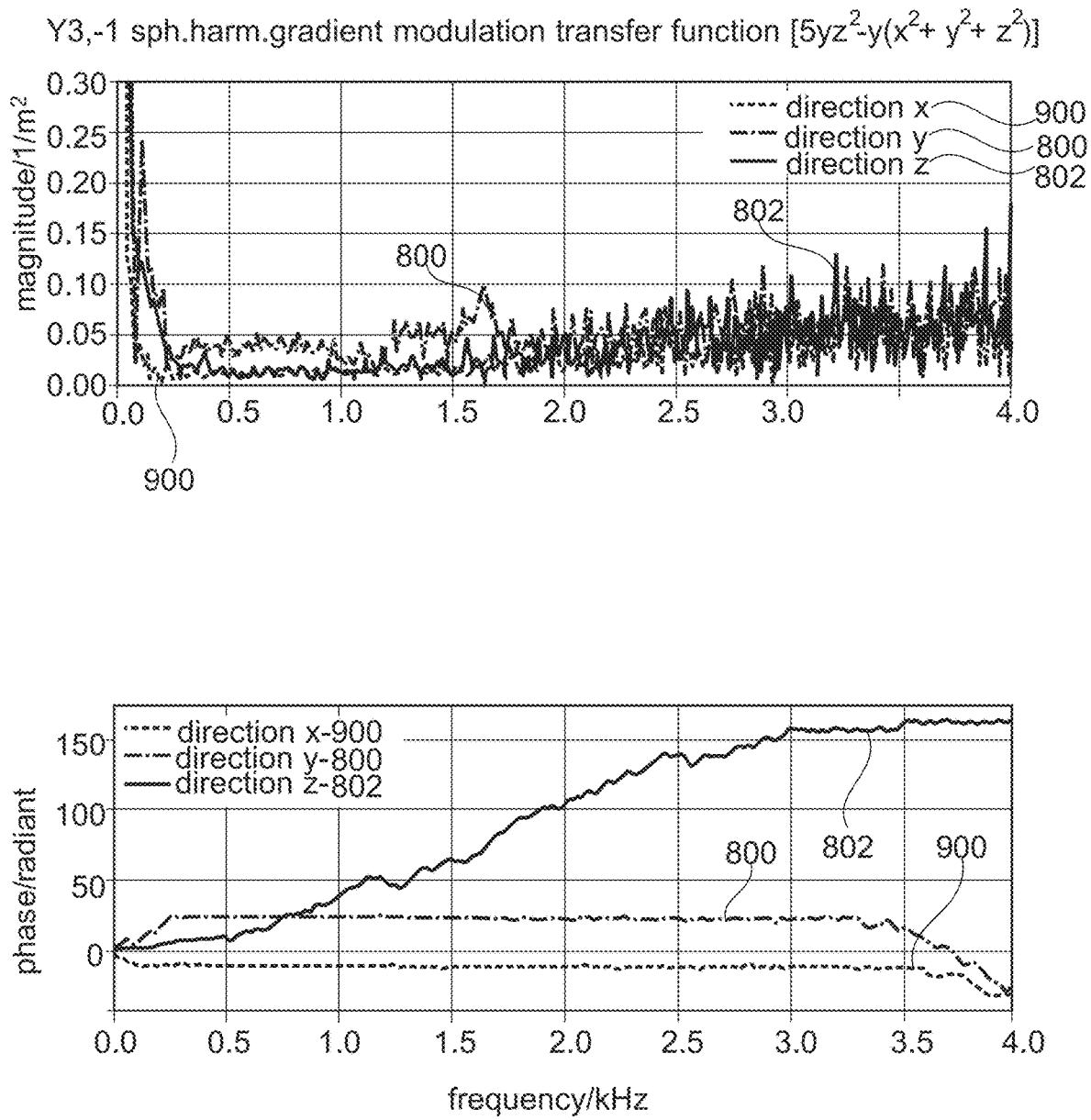
FIG. 12 plot of the phase and amplitude for the $Y_{-1}^3$ term of the gradient impulse transfer function for excitation on all three gradient channels.
Figure 13:
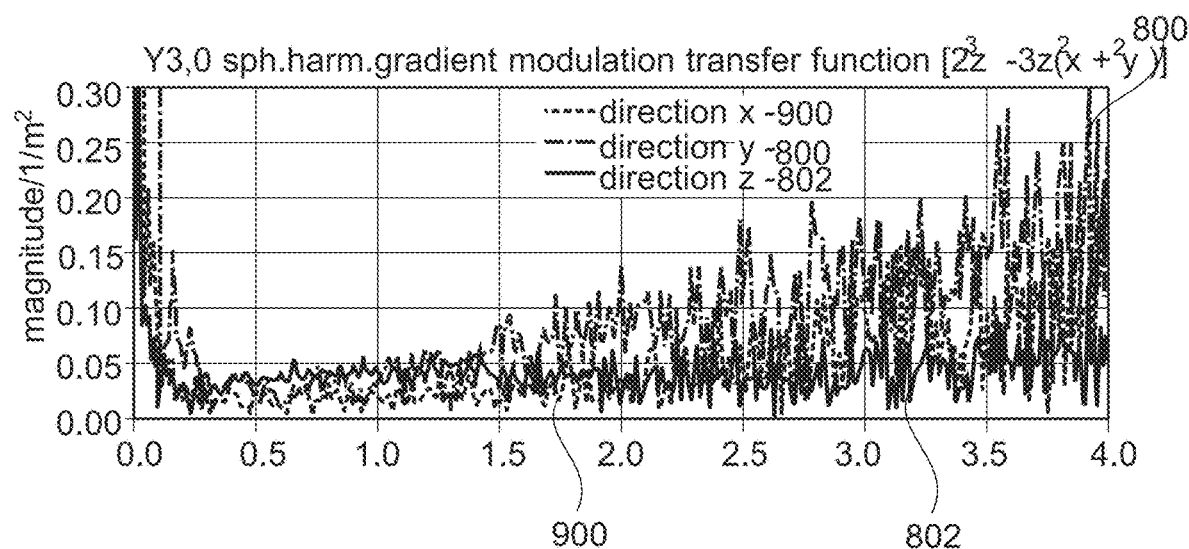
FIG. 13 plot of the phase and amplitude for the $Y_0^3$ term of the gradient impulse transfer function for excitation on all three gradient channels.
Figure 13:
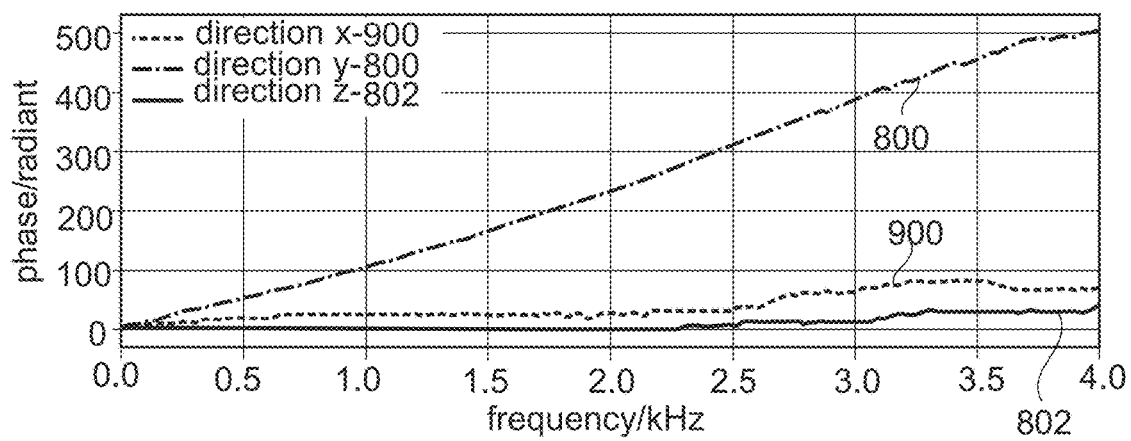
Figure 14:
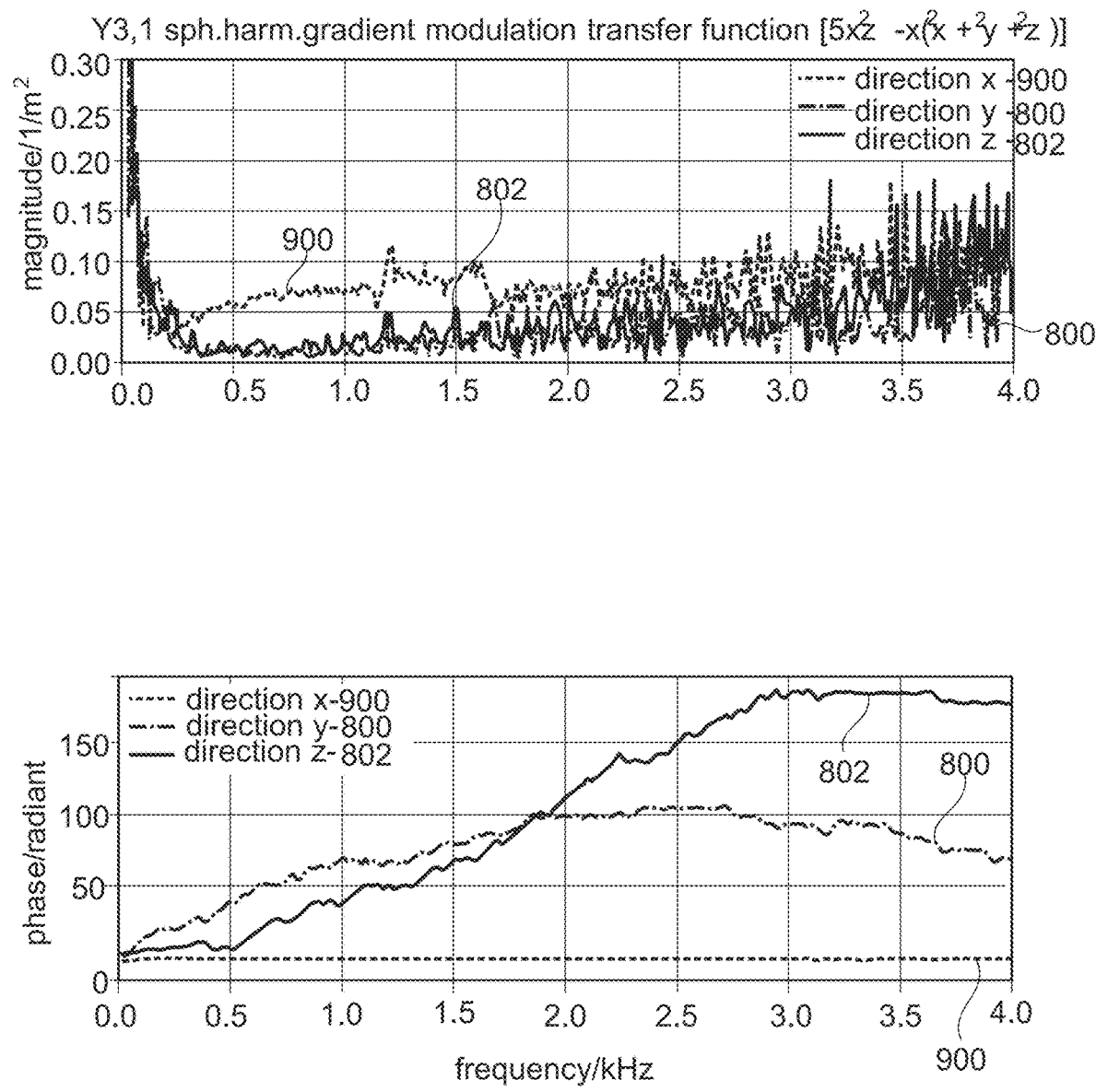
FIG. 14 plot of the phase and amplitude for the $Y_1^3$ term of the gradient impulse transfer function for excitation on all three gradient channels.

FIGS. 8 to 10 show linear cross terms orthogonal to the respective axes of excitation derived from a measurement with 4 slices and 5×5 phase encoding steps on a 3.0 Tesla system. "Direction" in the legend refers to the axis of gradient excitation, while the spherical harmonic term given in brackets in the graph titles denotes the spatial gradient term that it plotted. FIGS. 8, 9 and 10 shows the linear cross-terms orthogonal to the respective axes of excitation derived from a measurement with four slices and 5×5 phase encoding steps on the system shown in FIG. 7. FIG. 8 shows the magnitude and phase for the $Y_0^1$ spherical harmonics of the gradient modulation transfer function for the y-direction 800 and the z-direction 802. FIG. 9 shows the $Y_0^1$ spherical harmonics in both the magnitude and phase for the x-direction 900 and the z-direction 802. FIG. 10 shows the $Y_1^1$ spherical harmonic for the gradient modulation transfer function in the x-direction 900 and the y-direction 800 again for both phase and magnitude FIGS. 11 to 14 show GMTFs for selected higher order spherical harmonic terms derived from measurement with 5×5 phase encoding steps on the 3.0 Tesla system. FIG. 11 shows the gradient modulation transfer function for selected higher order spherical harmonics in terms of the measurements that were illustrated in FIGS. 7-10. These are all shown for the x-direction 900, y-direction 800 and z-direction 802. In FIGS. 11-14 both values for magnitude and phase are shown. FIG. 11 shows the $Y_0^2$ spherical harmonic, FIG. 12 shows the $Y_{-1}^3$ spherical harmonic, FIG. 13 shows the $Y_0^3$ spherical harmonic, and FIG. 14 shows the $Y_1^3$ spherical harmonic.

The information gained from 3D gradient system characterization can be used for improving gradient coil design. It can also be used for improving system calibration (eddy current compensation), which is especially desirable when measuring with demanding gradient waveforms, such as in diffusion or non-Cartesian scans. Image reconstruction could be improved by using actual k-space coordinates calculated from GMTFs instead of using the nominal k-space trajectory.

Examples could be used as an add-on for customers requiring highest gradient fidelity (e.g. for non-Cartesian imaging) or become part of the standard calibration procedure of MRI systems.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 magnetic resonance imaging system
104 magnet
106 bore of magnet
108 imaging zone
109 region of interest
110 set of gradient coils
112 magnetic field gradient coil amplifier
113 current sensor system
114 body coil
115 surface coil
116 transceiver
118 phantom
120 subject support
122 z-axis
124 slice
124' slice
126 computer system
128 hardware interface
130 processor
132 user interface
134 computer memory
140 machine executable instructions
142 calibration pulse sequence commands
144 magnetic resonance calibration data
146 Fourier transform of magnetic resonance calibration data
148 expansion of the fourier transfored magnetic resonance calibration data into spherical harmonics
150 three-dimensional gradient impulse response function
200 repeatedly control the magnetic resonance imaging system with the calibration pulse sequence commands to acquire the magnetic resonance calibration data for multiples slices using at least one of the three orthogonal gradient coils to generate the slice select gradient magnetic field
202 compute a Fourier transform of the magnetic resonance calibration data for each of the voxels of the multiple slices in phase encoding directions
204 compute an expansion of the Fourier transformed magnetic resonance calibration data into spherical harmonics
206 calculate a three-dimensional gradient impulse response function for the at least one of the three orthogonal gradient coils using the expansion into spherical harmonics
300 subject
320 imaging pulse sequence commands
322 magnetic resonance imaging data
324 magnetic resonance image
400 medical instrument
402 medical apparatus
404 additional region
406 control commands
500 thin slice approach
502 thin slice approach with 2D phase encoding
504 slice select direction
506 first phase encoding direction
508 second phase encoding direction
600 slice select gradient pulse
602 readout gradient pulse
604 phase encoding gradient pulses
700 photograph of phantom in MR system
702 digram showing slice selection.
800 y direction
802 z direction
900 x direction

The invention claimed is:

1. A medical instrument comprising a magnetic resonance imaging system with an imaging zone, wherein the magnetic resonance imaging system comprises:

a gradient coil system for generating a gradient magnetic field within the imaging zone, wherein the gradient coil system comprises three orthogonal gradient coils;

a memory for storing machine executable instructions and calibration pulse sequence commands, wherein the calibration pulse sequence commands are configured for acquiring magnetic resonance calibration data from a magnetic resonance imaging phantom within the imaging zone according to a calibration magnetic resonance imaging protocol with two-dimensional phase encoding perpendicular to a slice select gradient magnetic field, wherein the calibration magnetic resonance imaging protocol is configured for acquiring slices divided into voxels by the two-dimensional phase encoding;

a processor for controlling the magnetic resonance imaging system, wherein execution of the machine executable instructions causes the processor to:

repeatedly control the magnetic resonance imaging system with the calibration pulse sequence commands to acquire the magnetic resonance calibration data for multiples slices using at least one of the three orthogonal gradient coils to generate the slice select gradient magnetic field;

compute a Fourier transform of the magnetic resonance calibration data for each of the voxels of the multiple slices in the phase encoding directions;

compute an expansion of the Fourier transformed magnetic resonance calibration data into spherical harmonics; and calculate a three-dimensional gradient impulse response function for the at least one of the three orthogonal gradient coils using the expansion into spherical harmonics.

2. The medical instrument of claim 1, wherein the memory further contains imaging pulse sequence commands for acquiring magnetic resonance imaging data from the imaging zone according to an imaging magnetic resonance imaging protocol, wherein execution of the machine executable instructions further causes the processor to:

control the magnetic resonance imaging system with the imaging pulse sequence commands to acquire the magnetic resonance imaging data; and reconstruct a magnetic resonance image from the magnetic resonance imaging data.

3. The medical instrument of claim 2, wherein the reconstruction of the magnetic resonance image comprises correcting the magnetic resonance image using higher order terms of the three-dimensional gradient impulse function.

4. The medical instrument of claim 2, wherein execution of the machine executable instructions further causes the processor to correct the imaging pulse sequence commands using the three-dimensional gradient impulse response function for the at least one of the three orthogonal gradient coils by driving orthogonal gradient coils for suppression of cross terms or by adjusting higher order shim coils for the suppression of unwanted higher order response terms.

5. The medical instrument of claim 1, wherein the magnetic resonance imaging comprises a radio frequency system with multiple receive coils.

6. The medical instrument of claim 5, wherein the calibration magnetic resonance imaging protocol is a SENSE magnetic resonance imaging protocol using the multiple receive coils.

7. The medical instrument of claim 5, wherein execution of the machine executable instructions causes the processor to adjust a number of the multiple slices and a number of two-dimensional phase encoding steps according to a planned magnetic resonance imaging protocol.

8. The medical instrument of claim 1, wherein the calibration pulse sequence commands are configured for exciting two or more of the multiples slices simultaneously using multi-band thin-slice excitation.

9. The medical instrument of claim 1, wherein the magnetic resonance imaging system comprises a dedicated receive coil that is used for acquiring the magnetic resonance calibration data to account for effects of the dedicated receive coil in the three-dimensional gradient impulse response function.

10. The medical instrument of claim 1, wherein execution of the machine executable instructions further causes the processor to receive a B0 homogeneity map of the imaging zone, wherein the computation of the Fourier transform of the magnetic resonance calibration data for each voxel of the multiple slices in phase encoding directions is corrected using the B0 homogeneity map.

11. The medical instrument of claim 1, wherein the medical instrument further comprises any one of the following: a nuclear medicine imaging system, a positron emission tomography system, a single photon emission tomography system, a computed tomography imaging system, a radio therapy system, and a LINAC system.

12. The medical instrument of claim 1, wherein the calibration magnetic resonance imaging protocol is any one of the following: a thin slice magnetic resonance imaging protocol, a gradient pulse magnetic resonance imaging protocol, and combinations thereof.

13. The medical instrument of claim 12, wherein the gradient pulse magnetic resonance imaging protocol comprises a read out gradient generated by the slice select gradient, wherein the read out gradient is any one of the following: a chirp read out gradient, a triangular read out gradient, an alternating combination of a chirp readout gradient and a triangular read out gradient, and a dedicated waveform computed to achieve maximal spectral intensity at a chosen bandwidth of interest.

14. A method of operating a medical instrument comprising a magnetic resonance imaging system with an imaging zone, wherein the magnetic resonance imaging system comprises a gradient coil system for generating a gradient magnetic field within the imaging zone, wherein the gradient coil system comprises three orthogonal gradient coils, wherein the method comprises:

repeatedly controlling the magnetic resonance imaging system with calibration pulse sequence commands to acquire the magnetic resonance calibration data for multiples slices using at least one of the three orthogonal gradient coils to generate the slice select gradient magnetic field, wherein the calibration pulse sequence commands are configured for acquiring magnetic resonance calibration data from a magnetic resonance imaging phantom within the imaging zone according to a calibration magnetic resonance imaging protocol with two-dimensional phase encoding perpendicular to a slice select gradient magnetic field, wherein the calibration pulse sequence commands are configured for acquiring slices divided into voxels by the two-dimensional phase encoding;

computing a Fourier transform of the magnetic resonance calibration data for each of the voxels of the multiple slices in the phase encoding directions;

computing an expansion of the Fourier transformed magnetic resonance calibration data into spherical harmonics; and calculating a three-dimensional gradient impulse response function for the at least one of the three orthogonal gradient coils using the expansion into spherical harmonics.

15. A computer program product comprising machine executable instructions for execution by a processor configured for controlling a medical instrument, wherein the medical instrument comprises a magnetic resonance imaging system with an imaging zone, wherein the magnetic resonance imaging system comprises a gradient coil system for generating a gradient magnetic field within the imaging zone, wherein the gradient coil system comprises three orthogonal gradient coils, wherein execution of the machine executable instructions causes the processor to:
- repeatedly control the magnetic resonance imaging system with the calibration pulse sequence commands to acquire magnetic resonance calibration data for multiples slices using the at least one of the three orthogonal gradient coils to generate the slice select gradient magnetic field, wherein the calibration pulse sequence commands are configured for acquiring magnetic resonance calibration data from a magnetic resonance imaging phantom within the imaging zone according to a calibration magnetic resonance imaging protocol with two-dimensional phase encoding perpendicular to a slice select gradient magnetic field, wherein the calibration magnetic resonance imaging protocol is configured for acquiring slices divided into voxels by the two-dimensional phase encoding;
- compute a Fourier transform of the magnetic resonance calibration data for each of the voxels of the multiple slices in the phase encoding directions;
- compute an expansion of the Fourier transformed magnetic resonance calibration data into spherical harmonics; and
- calculate a three-dimensional gradient impulse response function for the at least one of the three orthogonal gradient coils using the expansion into spherical harmonics.

* * * * *